(12) United States Patent
Vistisen et al.

(10) Patent No.: US 12,352,748 B2
(45) Date of Patent: Jul. 8, 2025

(54) LATERAL FLOW ASSAY DEVICE AND ANALYSER

(71) Applicant: Foss Analytical A/S, Hilleroed (DK)

(72) Inventors: Rasmus Vistisen, Hilleroed (DK); Jakob Frederik Schoendorff Engell, Hilleroed (DK)

(73) Assignee: FOSS Analytical A/S, Hilleroed (DK)

( * ) Notice: Subject to any disclaimer, the term of this patent is extended or adjusted under 35 U.S.C. 154(b) by 1118 days.

(21) Appl. No.: 17/270,981

(22) PCT Filed: Aug. 7, 2019

(86) PCT No.: PCT/IB2019/056709
§ 371 (c)(1),
(2) Date: Feb. 24, 2021

(87) PCT Pub. No.: WO2020/058782
PCT Pub. Date: Mar. 26, 2020

(65) Prior Publication Data
US 2021/0255182 A1 Aug. 19, 2021

(30) Foreign Application Priority Data
Sep. 21, 2018 (DK) .............................. PA201800619

(51) Int. Cl.
*G01N 33/543* (2006.01)
*B01L 3/00* (2006.01)

(52) U.S. Cl.
CPC ........ *G01N 33/54388* (2021.08); *B01L 3/508* (2013.01); *B01L 2300/04* (2013.01);
(Continued)

(58) Field of Classification Search
CPC ...... G01N 33/54388; G01N 2021/7759; B01L 3/508; B01L 2300/04; B01L 2300/0609;
(Continued)

(56) References Cited

U.S. PATENT DOCUMENTS

| 5,591,401 A | 1/1997 | Sayles |
| 6,074,606 A | 6/2000 | Sayles |

(Continued)

FOREIGN PATENT DOCUMENTS

| EP | 1459040 B1 | 5/2017 |
| WO | WO-2007137257 A2 | 11/2007 |

(Continued)

OTHER PUBLICATIONS

International Search Report for International Application No. PCT/IB2019/056709 dated Dec. 2, 2019.

(Continued)

*Primary Examiner* — Samuel P Siefke
(74) *Attorney, Agent, or Firm* — Harness, Dickey & Pierce, P.L.C.

(57) ABSTRACT

A device comprises: a receptacle having a bottom wall portion closing a first end of the receptacle to delimit an inner space and having a receptacle opening at an opposite second end; a compartment for holding a lateral flow assay test strip, the compartment having a lower portion located closer to the first end than to the second end; a passageway in fluid communication with the lower portion of the compartment; and a lid configured to overlay the receptacle opening and comprising a body portion. A sample receiving portion is located in said body portion and is arranged in fluid communication with the inner space. The liquid passageway is delimited by a first opening into the lower portion of the compartment and a second opening in the lid.

20 Claims, 4 Drawing Sheets

(52) U.S. Cl.
CPC .............. *B01L 2300/0609* (2013.01); *B01L 2300/0681* (2013.01); *B01L 2300/0825* (2013.01)

(58) Field of Classification Search
CPC ..... B01L 2300/0681; B01L 2300/0825; B01L 3/50825; B01L 2300/047; B01L 3/5023
See application file for complete search history.

(56) References Cited

U.S. PATENT DOCUMENTS

| | | | |
|---|---|---|---|
| 7,244,392 B1* | 7/2007 | Konecke | A61B 10/007 436/166 |
| 8,394,626 B2 | 3/2013 | Ramsey et al. | |
| 9,949,724 B2* | 4/2018 | Hartselle | B01L 3/508 |
| 2004/0132091 A1 | 7/2004 | Ramsey et al. | |
| 2004/0133128 A1* | 7/2004 | Guan | B01L 3/502 600/584 |
| 2006/0029517 A1 | 2/2006 | Hartselle | |
| 2007/0196234 A1* | 8/2007 | Huff | G01N 33/493 422/400 |
| 2007/0196240 A1 | 8/2007 | Boozer et al. | |

FOREIGN PATENT DOCUMENTS

| | | |
|---|---|---|
| WO | WO-2012150544 A1 | 11/2012 |
| WO | WO-2018055432 A1 | 3/2018 |

OTHER PUBLICATIONS

Written Opinion for International Application No. PCT/IB2019/056709 dated Dec. 2, 2019.

Danish Search Report for Danish Application No. PA 2018 00619 dated Mar. 15, 2019.

* cited by examiner (a)

LATERAL FLOW ASSAY DEVICE AND ANALYSER

CROSS-REFERENCE TO RELATED APPLICATIONS

This application is a national phase under 35 U.S.C. § 371 of PCT International Application No. PCT/IB2019/056709 which has an International filing date of Aug. 7, 2019, which claims priority to Danish Application No. PA201800619, filed Sep. 21, 2018, the entire contents of each of which are hereby incorporated by reference.

The present invention relates to a device for performing a lateral flow assay and to an analyser incorporating the same.

Generally, lateral flow assays are performed using test strips in which a liquid sample to be analysed from a material of interest is placed at or near one short side of an elongate test strip ("liquid receiving zone" of the test strip). The sample is carried towards the opposite short side of the test strip by mobile, typically liquid, phase that traverses the test strip, usually by capillary action (or "wicking") but transport may be by other means, such as a pump. Typically, a portion of the test strip is pre-treated with a labelled reagent which preferentially binds to an analyte of interest, if present, in the sample. The bound reagent continues to propagate along the test strip together with any unbound reagent until they encounter a test zone which is pre-treated with an immobilised binding agent. The immobilised binding agent binds the bound reagent/analyte complexes and permits any unbound labelled reagent to continue to traverse the test strip and pass out of the test zone. The so bound complexes have a distinctive colour, may be stimulated to fluoresce or possess another detectable optical or non-optical property which can produce a signal indicative of the presence and/or concentration of analyte in the sample. The detectable signal can be measured, such as by an electrical reader, an optical reader or by visual inspection. The elongate test strip may comprise different layers or be provided with different test zones and/or reagent containing zones so that more than one analyte may be tested for using the same test strip. The test strip may be affixed to an impermeable support. The test strip may be formed such that labelled reagent is initially immobilised on the test strip at the reagent containing zone and remains immobilised there after binding to the analyte to be measured in a manner as described above. The reagent containing zone(s) will then also be the test zone. Indeed, the configuration of the test strip may be varied in many ways in dependence of the assay to be performed and for example include enzyme linked immunosorbent assays ("ELISA") test strip configurations.

Analyte testing using such lateral flow test strips very often require certain preparatory steps in order to obtain a sample from a material of interest. In particular, solid material, for example cereal, is often subject to an extraction procedure whereby the solid, usually having been processed to a granular solid, is mixed with an extraction liquid and typically forms a suspension. The mixture is allowed to undergo a chemical reaction whereby the analyte or analytes of interest are moved from the solid material and into the liquid phase. The liquid phase containing the analyte(s) must then be separated from the suspended solid and a precise quantity of the separated liquid introduced to the liquid receiving zone of the test strip as the sample to be analysed. Such preparatory steps are typically entirely or partially carried out manually and as such are both time consuming and error prone, to an extent that the lateral flow assay of solid material is often performed by trained laboratory technicians.

It is known, for example from WO 2012/150544, to provide a device for performing a lateral flow assay which comprises a receptacle that is closed at one end and open at an opposite end; a lid for closing the open end of the receptacle; a compartment for holding a lateral flow assay test strip and having a lower portion closer to the closed end than to the open end of the receptacle and a liquid passageway formed as a pump chamber of piston pump and having a first opening into the lower portion and a second opening into a side wall of the receptacle, the openings being sealable and un-sealable under the action of the piston pump to enable the transfer of a portion of the liquid in the receptacle to the lower portion of the compartment.

According to a first aspect of the present invention there is provided a device for performing a lateral flow assay comprising:
 a receptacle having a bottom wall portion closing a first end of the receptacle to delimit an inner material receiving space and having a receptacle opening at a second end of the receptacle opposite the first end;
 a compartment for holding a lateral flow assay test strip, the compartment having a lower portion located closer to the first end of the receptacle than the second end;
 a liquid passageway in fluid communication with the inner material receiving space and the lower portion; and
 a lid adapted to overlay the receptacle opening and comprising a body portion having an outer periphery; wherein
 a sample receiving portion is located in said body portion and is arranged in liquid communication with the inner material receiving space; and wherein
 the liquid passageway is delimited by a first opening into the lower portion of the compartment and a second opening in the lid.

Thus a filtered liquid sample may be transferred from the inner material receiving space to a lower part of the compartment holding a lateral flow test strip which will be orientated in use with its liquid receiving zone at the lower portion so that in use flow of sample along the lateral flow test strip will be upwards, against gravity. In this manner the sample becomes distributed more evenly across the width of the lateral flow device as it progresses laterally as would be the case if the lateral flow is in a direction with gravity.

In some embodiments the body portion may also house a sample well having a well opening in liquid communication with the sample receiving portion at a location closer to the outer periphery of the body portion than the sample receiving portion and preferably accessible form external the lid. A fixed volume of a liquid sample may then be collected in the sample well for eventual transfer to the second opening of the liquid passageway.

In some embodiments the body portion may also house a container having a container opening which in some embodiments may be permanently open or which in other embodiments may be initially overlaid and closed by a liquid impermeable barrier. In the latter embodiments the liquid impermeable barrier may be constructed of a frangible material which, when broken or penetrated, permits access to the container.

The container may comprise components or analytes which are desired for affecting the sample. Thus, the container may contain therein analytes or other components, such as reactive surfaces or beads, for performing e.g. a chemical reaction in or with the sample or otherwise converting the sample or a portion thereof before transfer of the sample into the liquid passageway.

In some embodiments the lid may also comprise a filter and/or seal disposed to cover at least a section of the sample receiving portion. This filter and/or seal may advantageously prevent spilling of material to be sampled and/or of other material located in the inner material receiving space of the receptacle. The filter may be used for separating the material from the inner material receiving space into a filtered fraction which forms the sample allowed to reach the well opening and another fraction retained in the receptacle. In some embodiments the filter may cover the open top and in others the filter may be carried by the lid.

In some embodiments the lid may be adapted to provide a permanent closure of the open top of the receptacle, even being formed integrally therewith to provide a fixed permanent closure. In other embodiments the lid may be adapted to provide a temporary closure over the receptacle's open top. The latter embodiments have advantages that a single receptacle may be produced that can be employed for different purposes depending on the type of lid with which it is collocated, this may reduce manufacturing costs of the receptacle; also the receptacle may be reusable, thus reducing cost of ownership.

The present device is especially suited for rotation around a longitudinal axis which passes in a direction between the bottom wall portion of the receptacle and its open top in order to derive a fraction of material in the receptacle which is forced upwardly through the sample receiving portion and any filter, if present, under the influence of centrifugal force to form a sample. This has an advantage that liquid is already filtered to some degree by the effects of the centrifugal force before it passes through the filter. This reduces the possibility of the filter becoming clogged with large amounts of relatively large particles in suspension.

A portion of the sample then enters the compartment via the passageway. Naturally, the material in the receptacle need not have different fractions with different densities, for example, in which case the portion of the material which is forced upwardly to form the sample is identical to the material remaining in the receptacle.

In other embodiments the inner material receiving space is adapted to provide a variable volume, the reduction thereof, such as by squeezing it or by moving the bottom wall section thereof towards the open top, then causes the liquid in the receptacle to move towards and through the sample receiving portion of the lid. In some embodiments more fluid, for example a gas, could be added to reduce the volume available to the flowable fluid material in the inner material receiving space and thereby achieve the same movement effect. In the foregoing embodiments the relative longitudinal positions (positions projected along the longitudinal axis) of the sample receiving portion and the sample well are selected so that the liquid from the receptacle, forced upwardly and radially, leaves the sample receiving portion and some of it enters the sample well if present to form a sample. Then, the sample receiving portion may extend farther radially than the sample well, as long as the well opening is positioned correctly.

In some embodiments the second opening of the liquid passageway may connect directly with the sample receiving portion, in others it may be independent of and in liquid isolation from any other opening or orifice in the body portion of the lid and accessible only from external of the lid.

In one embodiment, the compartment for holding a lateral flow assay test strip comprises an elongate, oblong channel having its long edges extending in a direction between the first and the second ends of the receptacle and isolated from the inner material receiving space. An elongate, oblong lateral flow assay test strip is already or will be located in this compartment. The elongate test strip may be an element exhibiting a change in a parameter depending on the presence or a concentration of a component (analyte) of a liquid added thereto. A typical type of elongate lateral flow assay test strip suitable for use in the present invention is a dip stick or a immunoassay lateral flow device, comprising at least a portion capable of transporting liquid therein by capillary forces. Alternatively, liquid may be transported laterally along the test strip using a pump. Capillary forces may be created when the test strip comprises a bibulous woven or non-woven portion. Many alternatives exist, such as paper-like materials or hydrophilic or lipophilic materials or the like-depending on the sample or liquid type to be transported. This portion may then comprise therein or thereon at a test zone of the strip a chemical substance causing a reaction visible to an observer or to a measuring instrument. The portion capable of transporting liquid preferably exists all along the length of the elongate test strip and may be affixed to support, such as a liquid impermeable support.

The test zone of the elongate test strip, or a portion thereof or a material held thereby, may be capable of changing a colour, or another optical property, such as an absorption, transmission, reflection or another parameter which may be detected optically, such as when forming a chemical bond, the vibration thereof may be detected.

Other detectable parameters may be detected electronically, such as by a current generated or a current transported through the elongate sampling element. The device for performing a lateral flow assay may comprise electrodes capable of feeding a current to or through the elongate test strip.

In addition or alternatively, the compartment may comprise a window of a radiation transparent element or formed as a slot and located between the channel and the surroundings at least in the region of the test zone of the lateral flow assay test strip when placed in the compartment so that a colour change or a reflection/absorption/scattering or other optically detectable parameter may be detected by feeding radiation to the test zone and/or receiving radiation therefrom.

The compartment may be openable, such as may be achieved by forming the compartment as an open channel having a removable cover. The elongate test strip may then be provided therein, removed therefrom or replaced therein. Alternatively, the compartment may be sealed with the test strip located therein to prevent degradation, contamination or loss of the test strip. In the latter alternative the device is then a one-time use device. In some embodiments the compartment may be configured as a separate cartridge containing the lateral flow assay test strip and which is attachable to either or both the receptacle and the lid.

According to a second aspect of the present invention there is provided an analyser comprising:
  a device according to the first aspect of the present invention;
  a rotator adapted to rotate the device along a longitudinal axis passing centrally of the device in a direction between the first and the second ends of the receptacle; and
  a measuring instrument adapted to detect analyte induced changes in the test strip at the test zone thereof.

In some embodiments the analyser includes a dosing apparatus comprising a pipette system configured to transport liquid between wells and openings in the lid, particularly between a sample well, via any container, and to the second opening. Thus by using the device according to the first aspect of the present invention in the analyser of the second aspect sample separation and analyte detection may be made more automatic.

Although some aspects of embodiments of the present invention are summarised above it will be appreciated that this summary is not intended to limit the present invention, the scope of which is to be properly determined by the appended claims.

Exemplary embodiments comprising the present invention are described in greater detail below with reference to the drawings of the accompanying figures, of which:

FIG. 1 illustrates (a) a top view of an embodiment of a device according to the present invention; (b) a side view of the embodiment of FIG. 1 (a);

Elements which are common to two or more of the figures will be identified in those figures with the same reference numerals.

In FIGS. 1(a) and 1(b) an exemplary embodiment of a device 2 for performing a lateral flow assay is illustrated and comprises a receptacle 4; a lid 6; a compartment 8 and a liquid passageway 10 (broken line construction).

The receptacle 4 is constructed with an elongate side wall portion 12, which here is generally cylindrical, closed at a first end by a bottom wall portion 14 to delimit an inner material receiving space 16. The receptacle 4 has a receptacle opening 18 at a second end opposite the first end and the bottom wall portion 14 for accessing the inner material receiving space 16. The receptacle opening 18 may provide a single opening that is generally co-extensive with the second end of the receptacle (as illustrated) or may provide one or more sub-openings into the sample receiving space 16, which sub-openings together constitute the receptacle opening 18.

The lid 6 comprises a body 20 having an outer periphery 22 and in which is located a sample receiving portion 24 for liquid communication with the inner material receiving space 16 and a second opening 26 of the liquid passageway 10. The second opening 26 being located closer to the outer periphery 22 than the sample receiving portion 24. In the present embodiment a sample well 28 having a well opening 30 which is in liquid communication with the sample receiving portion 24 and which is located in the body 20 closer to its outer periphery 22 than the sample receiving portion. An optional collecting track 32 is provided which is arranged to direct fluid from the sample receiving portion 24 towards the well opening 30.

In the present embodiment the second opening 26 is located in the body 20 of the lid 6 above (in a direction from the bottom wall portion 14) the well opening 30 so that a portion 21 of the body 20 acts as an impermeable barrier to prevent liquid from the sample receiving portion 24 entering the second opening 26. In other embodiments a temporary seal may be provided to cover this second opening 26 to replace or supplement the impermeable barrier formed by the body portion 21. The seal may be made temporary for example by making it penetrable, for example by a pipette, such as by having a sufficiently small layer thickness, or for example by adhering the seal to the lid 6 or a relevant portion thereof with a relatively weak adhesive.

Figure 1:
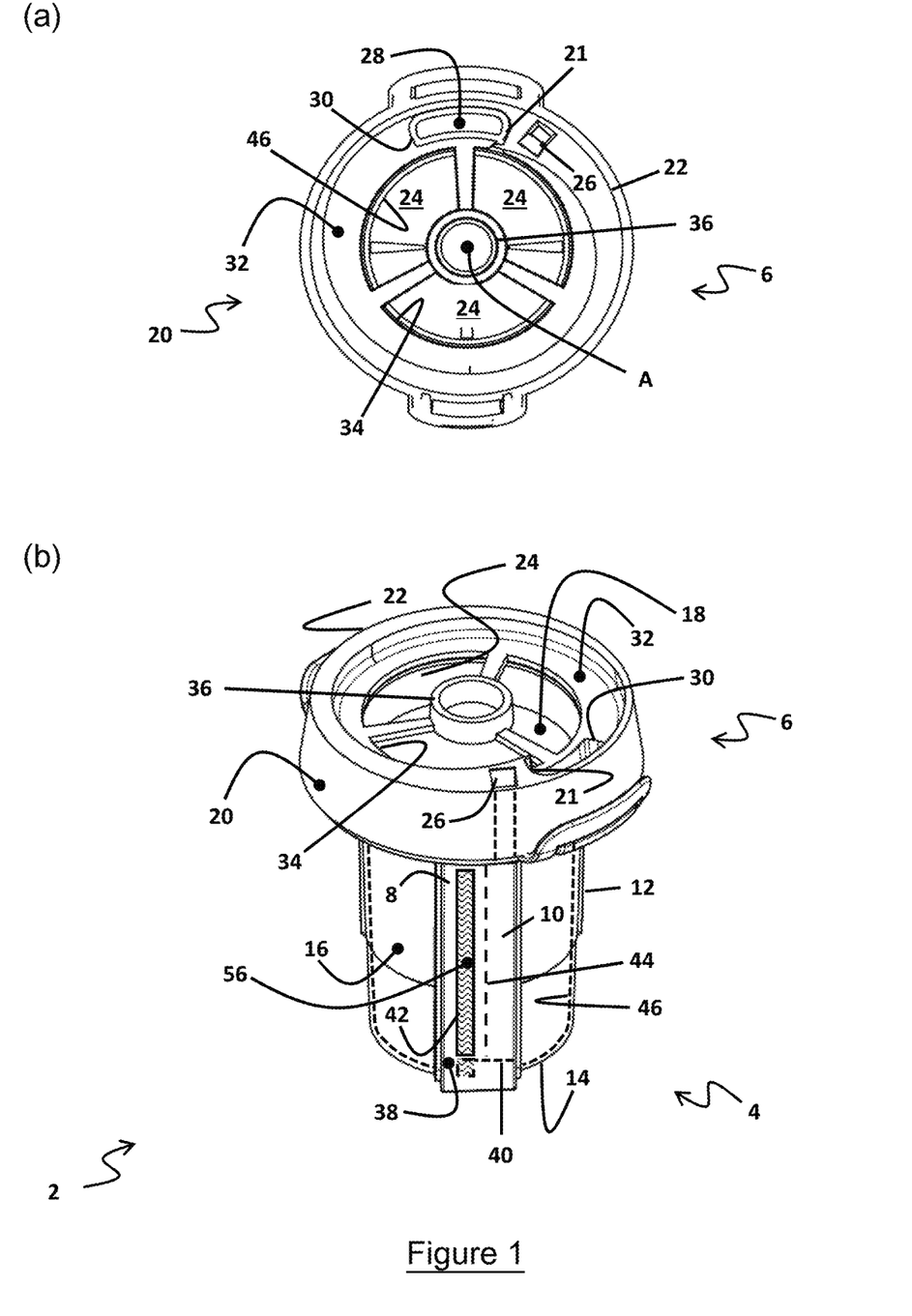

The body 20 is generally annular having an inner periphery 34 which here delimits the sample receiving portion 24 and which may be covered with a filter material (not shown in FIGS. 1). Filtering may be desired if a liquid present in the inner material receiving space 16 below the sample receiving portion 24 is a suspension of a solid and a liquid, where the solid is not desired in the sample well 28 or in the liquid passageway 10. In the present embodiment an optional centrally located through hole, here provided by a bore 36 is provided for external access to the inner material receiving space 16.

The compartment 8 is adapted to hold a lateral flow assay test strip (not illustrated in FIGS. 1) and comprises an oblong channel extending along the sidewall portion 12 of the receptacle 4 with a lower portion 38 provided in liquid communication with a first opening 40 of the liquid passageway 10. The compartment also comprises a window, here formed as a slot 42, dimensioned such that a test zone of a lateral flow assay test strip located in the oblong channel is made externally visible thereby when the test strip is orientated with its liquid receiving zone at the lower portion 38. In the present embodiment the liquid passageway 10 is an oblong channel running parallel with the oblong channel of the compartment 8 in abutment with and sharing a common long side 44.

In general, the device 2 is configured to be rotated around a longitudinal axis A which extends in a direction from the bottom wall portion 14 and through the lid 6, preferably centrally of the device 2. When the device 2 is so rotated at a sufficient speed a fluid, typically a liquid, present in the inner material receiving space 16 of the receptacle 4 below the lid 6 is forced outwardly and thus upwardly along a face 46 of sidewall portion 12 due to centrifugal force. This fluid is forced through the sample receiving portion 24 then outwardly towards the outer periphery 22 into the collecting track 32, which in the present embodiment flares outwardly away from the axis A to guide fluid from the sample receiving portion 24 towards the sample well opening 30. A liquid sample is thus collected in the sample well 28.

Subsequently liquid from the sample well 28 is transferred via the second opening 26 into the liquid passageway 10 in which it flows via the first opening 40 into the lower portion 38 of the compartment 8 to contact the liquid receiving zone of a lateral flow assay test strip that will be present in the compartment 8. In some embodiments a wick, such as may be formed of a paper; fibrous woven material or other bibulous material, may be provided connected between the first opening 40 and the lower portion 38 in order to facilitate liquid transportation from the passageway 10 to the compartment 8 (and hence the liquid receiving zone of a lateral flow assay test strip).

In the present embodiment the lid 6 is illustrated as already closing the second end of the receptacle 4. It will be appreciated that the lid 6 may be formed integrally with the receptacle 4 to provide a permanent closure. The lid 6 may in some embodiments may be separate from the receptacle 4 and be collocatable therewith in order to temporarily or permanently close the receptacle 4. It is intended that none of these alternatives are to be excluded from the scope of the invention as defined by the appended claims.

Figure 2:
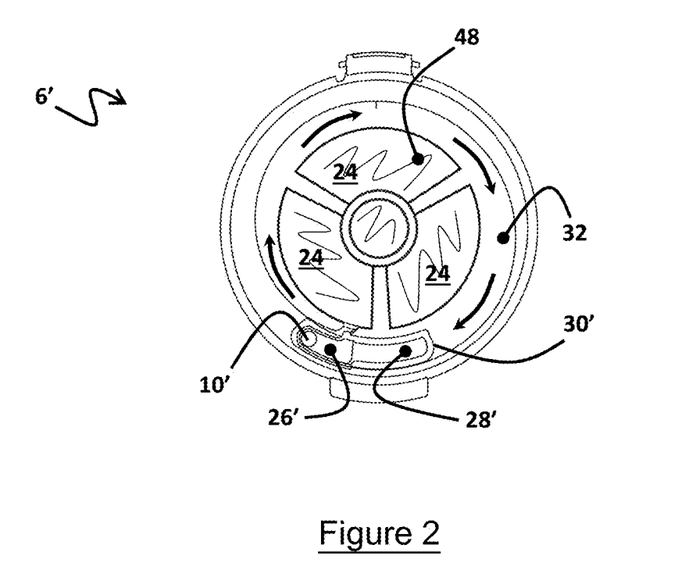
FIG. 2 illustrates a top view of an embodiment of a device according to the present invention.

FIG. 2 illustrates a further example of a lid 6' which may be used to close a receptacle opening of a device according to the present invention. Different from the lid 6 illustrated in FIGS. 1, the second opening 26' of a passageway 10' is located in liquid communication with the sample receiving portion 24 to receive liquid therefrom. The passageway 10' is analogous to that passageway 10 of the device 2 of FIG. 1.

Optionally, and illustrated in FIG. 2, a sample well 28' is also provided to collect liquid having passed through the sample receiving portion 24. A well opening 30' here lies at approximately the same height as the second opening 26'. A filter material 48 is shown to cover the sample receiving portion 24 as well as the central bore 36. Also illustrated by the arrows in this FIG. 2 is the direction of movement of liquid along the collecting track 32 as the lid 6' is rotated as described above together with a receptacle, such as the receptacle 4 of FIGS. 1, it closes.

Figure 3:
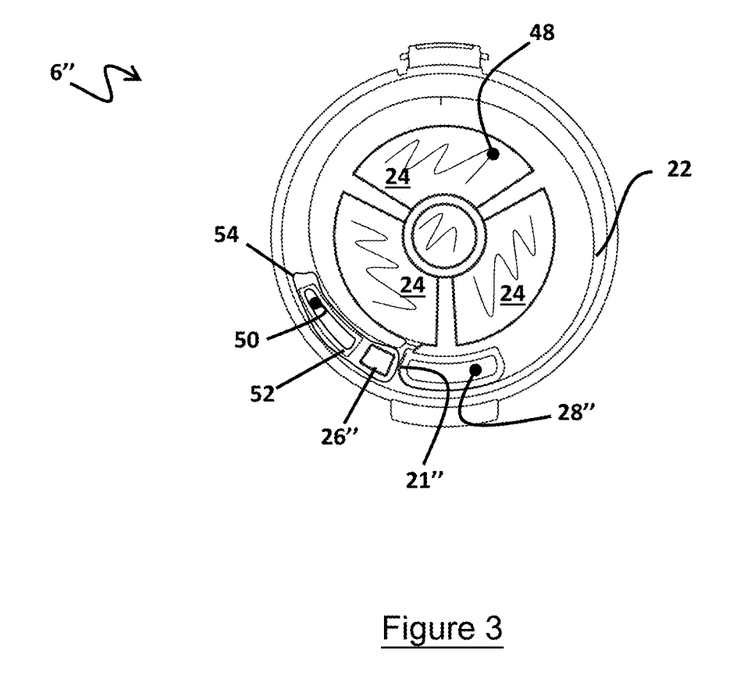
FIG. 3 illustrates a top view of an embodiment of device according to the present invention.

FIG. 3 illustrates a still further example of a lid 6" which may be used to close a receptacle opening of a device according to the present invention. Similar to the lid 6 illustrated in FIGS. 1, the lid 6" of the present exemplary embodiment has a second opening 26" located in the body 20" above a well opening 30" of a sample well 28" so that a body portion 21" forms a liquid impermeable barrier to inhibit the passage of liquid from the sample receiving portion 24 into the second opening 26". The second opening 26" delimits one end of a liquid passageway (not shown in this FIG. 3) which is functionally equivalent to those passageways 10, 10' described above with respect to the FIG. 1 and FIG. 2.

Different from the lid 6 illustrated in FIG. 1 and the lid 6' illustrated in FIG. 2, the lid 6" has a container 50 having a container opening 52. In the present example the container opening 52 is located at a same height as the second opening 26" so that the body portion 21" may also act as a liquid impermeable barrier to prevent entry of liquid from the sample receiving space 24. Additionally or alternatively a temporary seal 54 may overlay the container opening 52 and optionally also the second opening 26". This seal 54 then acts to prevent ingress of liquid into the container 50 and the egress of any material already contained in the container 50 until required. In some embodiments, including those described above, a seal may be provided to completely overlay the lid 6, 6', 6". As already mentioned above, the seal may be made temporary for example by making it penetrable, for example by a pipette, such as by having a sufficiently small layer thickness, or for example by adhering the seal to the lid 6 or a relevant portion thereof with a relatively weak adhesive.

The container 50 may comprise components or analytes which are desired for affecting liquid from the sample well 28". Thus, the container 50 may contain therein analytes or other components, such as reactive surfaces or beads, for performing e.g. a chemical reaction in or with liquid transferred from the sample well 28" or otherwise converting said liquid before transfer of the liquid or a portion thereof into the liquid passageway (not illustrated in this FIG. 3) via the second opening 26".

Figure 4:
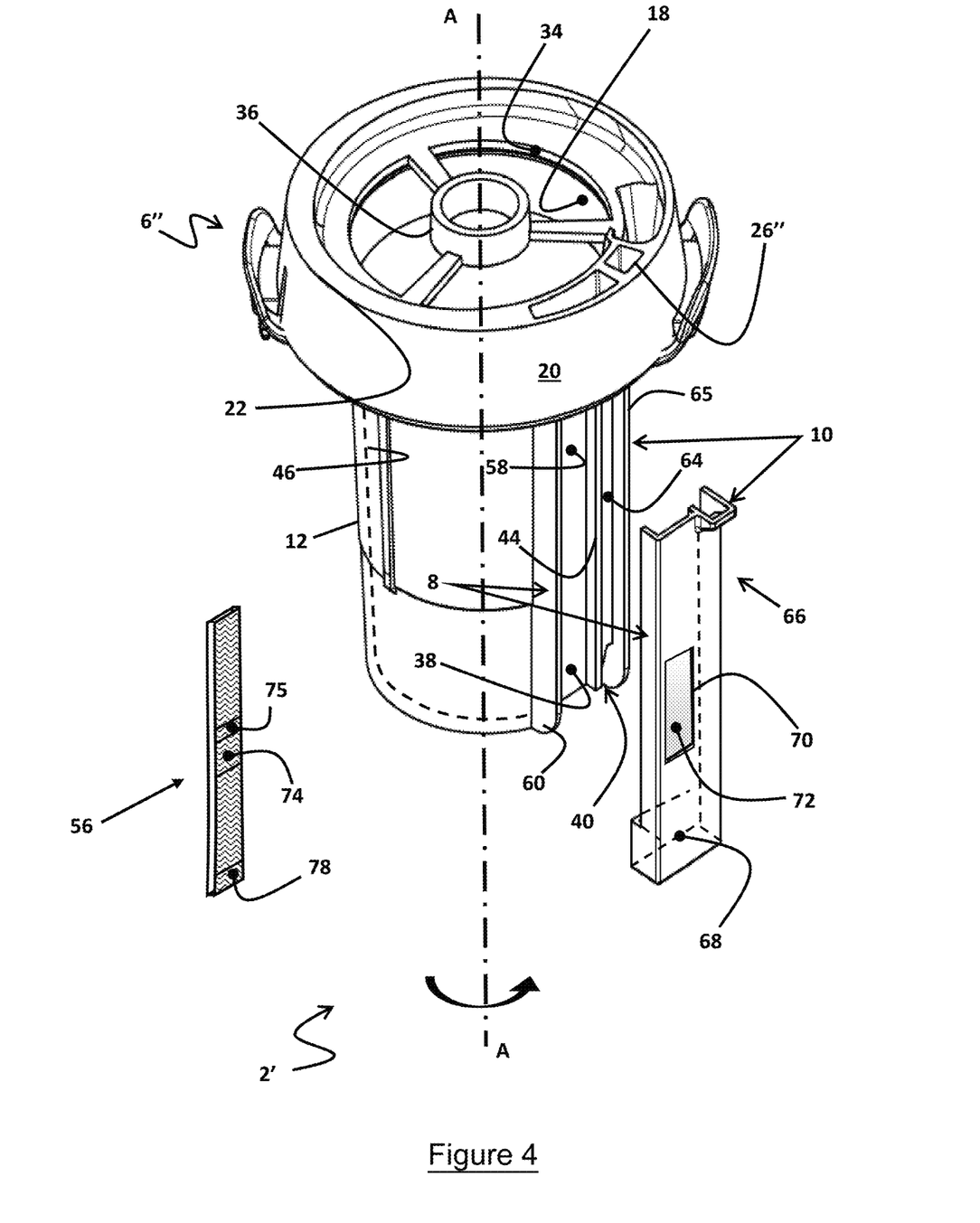
FIG. 4 illustrates an embodiment of a device according to the present invention.

In FIG. 4 a device 2' is shown as comprising a lid, here the lid 6" described above with reference to FIG. 3, and the receptacle 4 described above with reference to FIGS. 1.

The lid 6" closes the receptacle opening 18 at the second end of the receptacle 4 such that the sample receiving portion 24 overlays the receptacle opening 18 to provide liquid communication between the inner material receiving space 16 along the inner face 46 of elongate, generally cylindrical, side wall portion 12. Once so collocated, the second opening 26" in the lid 6" delimits one end of the passageway 10.

The compartment 8 for holding a lateral flow assay test strip 56 comprises an oblong channel 58 arranged with parallel long sides 44, 60 that extend along the sidewall portion 12 external of the receptacle 4 in a direction between the first end of the receptacle 4, defined by the bottom wall portion 14 and the opposing second end, at which the receptacle opening 18 is located and having the lower portion 38 closer to the bottom wall portion 14 than the receptacle opening 18.

The liquid passageway 10 is comprised of a substantially coextensive oblong channel 64 running parallel to the oblong channel 58 of the compartment 8 and has its first opening 40 adjacent the lower portion 38. The oblong channel 64 has an outer long side 65 and shares the long side 44 with the oblong channel 58 of the compartment 8.

A cover 66 is provided to enclose both oblong channels 58,64 to complete both the compartment 8 and the liquid passageway 10. A reservoir 68 is provided in the cover to connect the lower portion 38 of the compartment 8 with the liquid passageway 10 and may be considered as forming the first opening 40 of the liquid passageway 10. A window, here a slot 70 covered with a transparent layer 72 is provided in the cover 66 which is positioned so as to overlay a test zone 74 of the test strip 56 when the test strip 56 is located in the oblong channel 58 of the compartment 8 with its liquid receiving zone 78 located in the lower portion 38 of the channel 58. The cover 66 is preferably removable from overlaying the two channels 58,64 and may for example be configured for a sliding engagement with or a push fit over the outer long sides 60,65 of the compartment 8 and the liquid passageway 10 respectively. In some embodiments the compartment 8 and liquid passageway 10 may be formed as a unit that is removably collocatable with one or other of the receptacle 4 or the lid 6" to form an embodiment of the device (2' say) according to the present invention.

Figure 5:
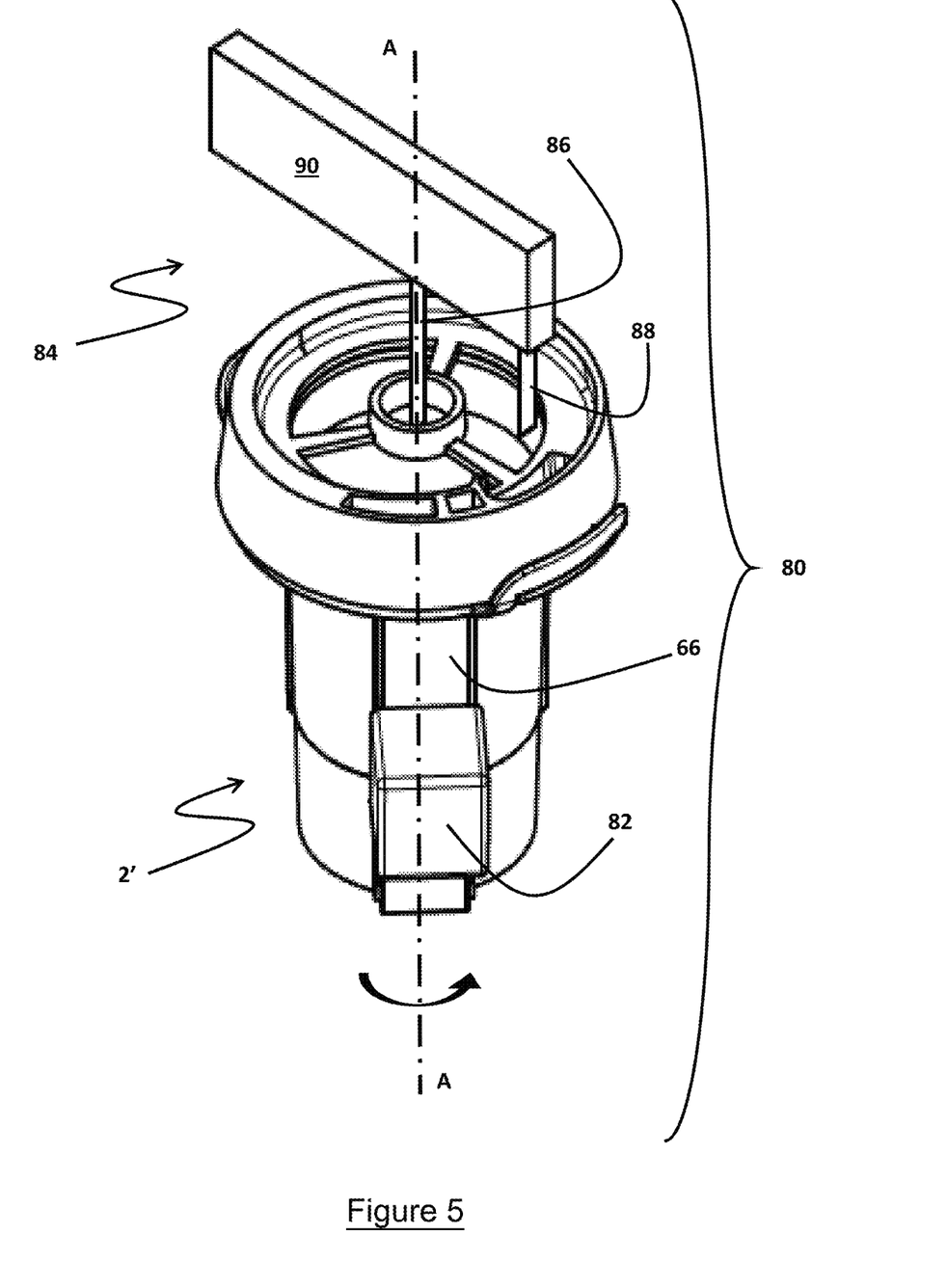
FIG. 5 illustrates an embodiment of an apparatus according to the present invention.

In FIG. 5 an apparatus 80 for performing a lateral flow assay is illustrated as comprising a device, here the device 2' described with reference to FIG. 4; a measuring instrument 82 adapted to detect analyte induced changes at the test zone 74 of the test strip 56; a dosing device 84 for transferring liquid into the second opening 26' (in the present embodiment from sample well 28" and via the container 50) and a rotator (not shown) adapted to rotate the device 2' around the longitudinal axis A in order to exert a centrifugal force on liquid in the receptacle 4 to move it through the sample receiving portion 24 of the lid 6" and into the sample well 28".

The measuring instrument 82 in the present embodiment comprises an illumination source and a detector arrangement (not shown) whereby the illumination source illuminates the test zone 74 of a test strip 56 located in the oblong channel 58 through the window 70,72 and the detector monitors the test zone 74 via the window 70,72 to detect optical effects caused by an analyte at the test zone 74. The illumination source of the measuring instrument 82 may comprise one or more different sources of optical radiation such as fluorescent tube, incandescent bulb, light emitting diode or laser. In some embodiments the illumination source may be an individual source of optical radiation, in others it may comprise an array of individual sources each selected to emit light of different wavelengths which may be singularly or severally selectively energisable in order to create a desired illumination of the target zone 74. In some embodiments the detector arrangement is positioned so that light from the illumination source that is reflected from the test zone 74 is detected by the detector arrangement. In other embodiments the detector arrangement is positioned so that light from the illumination source that is transmitted through the test zone 74 is detected by the detector arrangement. In still other embodiments the light from the illumination source may be selected to stimulate material at the test zone 74 to fluoresce when analyte is present and the detector arrangement is configured to detect this fluorescence. One measuring instrument suitable for use in the apparatus 80 described above is disclosed in EP 1 459 040, the contents of which incorporated herein in their entirety and which discloses an optical measuring device comprising an illumination device for illuminating a measuring plane, in which plane the test strip is to be placed; a planar image sensor; an optical system for imaging said measuring plane onto the image sensor; and an electronic evaluation unit for evaluation of the signals detected by said image sensor, said illumination device comprises light sources or other means of generating different colours which serve to alternatively illuminate said measuring plane in different colours, wherein said electronic evaluation unit detects the colouring of the test fields from the images obtained under different colour illuminations.

In some embodiments the test strip 56 may also comprise a reference zone 75, which is also monitored using the measuring instrument 82 and which, as illustrated in FIG. 4, may in some embodiments be located within the test zone 74, or at least adjacent the test zone 74 to be illuminated by the illumination source of the measuring instrument 82. This reference zone 75 is configured to provide a known reflectance (or transmission or fluorescence as appropriate) intensity on the detector arrangement the signal generated by which may be employed in the assessment of the signal generated from the test zone 74 dependent on the presence of an analyte there. It will be appreciated that the test strip 56 may comprise other control, reference and test zones to be monitored by the measuring instrument 82. It will be appreciated that the configuration and type of the measuring instrument 82 will be dependent on, amongst other things, the types of reagent used in the detection of the analyte(s) and on the location of binding moieties on the test strip.

The dosing devices 84 comprises two pipettes or needles 86,88 provided on a boom 90, where the pipette 86 is positioned directly above the central bore 36, such as on the longitudinal axis A, in order to dispense a liquid into the central bore 36 for transfer through the receptacle opening 18 into inner material receiving space 16 of the receptacle 4. The pipette 88 is positioned above the container opening 52 but may also be positioned above the well opening 30", by rotating the device 2' around the axis A (solid arrow). The rotator, such as a rotatable motor, (not illustrated) may be provided for rotating the device 2' around the axis A, which preferably is a symmetry axis of the device 2'. When spinning the sampling device 2' in order to urge material within the inner material receiving space 16 upwards along an inner surface 46 of side wall portion 12 by means of centrifugal force rotation speeds of several thousand revolutions per minute may be required. It is very useful then if the centre of mass of the sampling device 2' is located along the longitudinal axis A.

The boom 90, or preferably in some embodiments the individual pipettes 86,88, may be translated upwardly and downwardly, such as along the longitudinal axis A, which normally, at least during rotation of the device 2', is vertical. This simple translation and rotation nevertheless will allow the two pipettes 86,88 to both transfer liquid to the bore 36 as well as transfer liquid or the like between the sample well 28" and container 50 and between the container 50 and the second opening 26".

Thus, it is desired that the sample well 28", the container 50 and the second opening 26" may be engaged by the same pipette 88 simply by rotating the device 2' around the longitudinal axis A. Thus, the container opening 52, the well opening 30" and the second opening 26" should be accessible from above at the same distance from the axis A i.e. they should have an overlap in the direction perpendicular to the axis A (although of course circumferentially displaced from one another).

As described above, any resulting liquid from the container 50 or sample well 38" may be used for a measurement or a determination of properties thereof. Then, that liquid or the like is transferred from the well/container to the second opening 26" from where it travels via the passageway 10 to the liquid receiving zone 78 of a lateral flow assay test strip 56 located in the compartment 8.

A liquid dispensed via bore 36 into the receptacle 4 may be the liquid desired in the sample well 28" or may be one component of a liquid to be tested. The liquid in the receptacle 4 may be arrived at by e.g. mixing a liquid and another fraction, which may be solid, fluid, liquid or a mixture thereof, to the liquid to allow the mixture to react, if required. In one example, an extracting liquid is added into the receptacle 4, such as through the bore 36 via the pipette 86, which extracting liquid is selected to extract a component of interest from a cereal powder, which is the actual material to be tested and already present in the receptacle 4. Having allowed the extraction to take place, a portion of the resulting liquid will, when spinning the sampling device 2' around the axis A, pass through the sample receiving portion 24 via the filter 48 and arrive in the sample well 28", leaving the powder on the other side of the filter 48. In some uses it is envisaged that the lid (6" say) and the receptacle (4 say) are initially separate. The cereal powder to be tested is placed into the receptacle 4 and the lid 6' collocated therewith to close the receptacle 4. The so assembled sampling device 2' is then placed in the dosing apparatus 80, the extraction liquid dispensed into the receptacle 4 from the pipette 86 via the bore 36, and the sampling device 2' rotated rapidly around the longitudinal axis A.

The invention claimed is:

1. A device for performing a lateral flow assay, the device comprising:
   a receptacle having a bottom wall structure closing a first end of the receptacle to define an inner material receiving space and having a receptacle opening at a second end of the receptacle that is opposite to the first end of the receptacle;
   one or more first structures defining a compartment configured to hold a lateral flow assay test strip and having a lower portion that is located closer to the first end of the receptacle than to the second end of the receptacle;
   one or more second structure defining a liquid passageway having a first opening into the lower portion of the compartment, such that the liquid passageway is in fluid communication with the lower portion of the compartment; and
   a lid configured to overlay the receptacle opening, the lid including a body structure having an outer periphery, the body structure defining a sample receiving opening and a second opening of the liquid passageway the lid configured to position the sample receiving opening in fluid communication with the inner material receiving space based on the lid overlaying the receptacle opening.

2. The device according to claim 1, wherein the body structure defines the second opening as being in fluid communication with the sample receiving opening such that the second opening is configured to receive liquid from the sample receiving opening.

3. The device according to claim 1, wherein the one or more first structures includes a first oblong channel having long sides extending in a direction along the receptacle between the first end of the receptacle and the second end of the receptacle, wherein the first oblong channel is isolated from the inner material receiving space.

4. The device according to claim 3, wherein the one or more second structures includes a second oblong channel extending in parallel with and abutting one of the long sides of the first oblong channel of the compartment.

5. The device according to claim 4, wherein
the one or more first structures further includes a removable cover the removable cover further being included in the one or more second structures, the removable cover being configured to enclose both the first oblong channel and the second oblong channel to at least partially define both the compartment and the liquid passageway.

6. The device according to claim 5, wherein the removable cover is least partially defines a reservoir in fluid communication between the first opening of the liquid passageway and the lower portion of the compartment.

7. The device according to claim 1, wherein the one or more first structures defining the compartment includes a window configured to render an internal portion of the compartment visible from external to the compartment.

8. The device according to claim 1, wherein the body structure further defines a sample well that is closer to the outer periphery than the sample receiving opening, the sample well having a well opening accessible from external to the lid and in fluid communication with the sample receiving opening.

9. The device according to claim 8, wherein the body structure further defines
a liquid guide between the sample receiving opening and the well opening.

10. The device according to claim 8, wherein the body structure defines a container that is closer to the outer periphery than the sample receiving opening, the container having a container opening accessible from external to the lid.

11. The device according to claim 1 further comprising:
a lateral flow test strip having a liquid receiving zone, the lateral flow test strip being retained in the compartment such that the liquid receiving zone is proximate to and in fluid communication with the lower portion of the compartment.

12. The device according to claim 11, wherein
the one or more first structures includes a window through which the lateral flow test strip is visible external of the compartment, and
the lateral flow test strip has a test zone that overlaps with the window.

13. An apparatus for performing a lateral flow assay, the apparatus comprising:
the device as claimed in claim 1;
a rotator configured to rotate the device around a longitudinal axis passing centrally through the device in a direction between the first end of the receptacle and the second end of the receptacle; and
a measuring instrument configured to detect analyte induced changes in a lateral flow test strip at a test zone of the lateral flow test strip.

14. The apparatus according to claim 13, wherein
the body structure further defines a sample well that is closer to the outer periphery the sample receiving opening, the sample well having a well opening accessible from external to the lid and in fluid communication with the sample receiving opening; and
the apparatus further includes a dosing apparatus that includes a pipette system configured to transfer liquid between the sample well and the second opening.

15. The apparatus according to claim 14, wherein
the body structure defines a container that is closer to the outer periphery than the sample receiving opening, the container having a container opening accessible from external to the lid, and
the pipette system is configured to
transfer liquid from the sample well into the container, and
transfer the liquid from the container to the second opening.

16. The device of claim 8, wherein
the lid further includes a filter configured to cover at least a section of the sample receiving opening, the filter configured to separate material that is received at the filter from the inner material receiving space into
a filtered fraction which passes through the filter to reach the well opening, and
another fraction which is retained in the receptacle.

17. The device of claim 1, wherein the lid is separate from the receptacle and is configured to provide a temporary closure over the receptacle opening.

18. The device of claim 1, wherein at least a portion of the body structure of the lid defines a liquid impermeable barrier configured to inhibit liquid passage from the sample receiving opening into the second opening.

19. A device for performing a lateral flow assay, the device comprising:
a receptacle including a bottom wall structure closing a first end of the receptacle to define an inner material receiving space and having a receptacle opening at a second end of the receptacle that is opposite to the first end of the receptacle;
one or more first structures defining a compartment configured to hold a lateral flow assay test strip and having a lower portion that is located closer to the first end of the receptacle than to the second end of the receptacle; and
one or more second structures defining a liquid passageway having a first opening into the lower portion of the compartment, such that the liquid passageway is in fluid communication with the lower portion of the compartment,
wherein the receptacle is attachable to a lid, the lid including a body structure having an outer periphery and defining a sample receiving opening and a second opening,
wherein the receptacle is attachable to the lid such that the receptacle opening overlays the lid to cause the inner material receiving space to be in fluid communication with the sample receiving opening and to further cause the liquid passageway to be in fluid communication with the second opening.

20. A cartridge for performing a lateral flow assay, the cartridge comprising:
one or more first structures defining a compartment configured to hold a lateral flow assay test strip and having a lower portion; and
one or more second structures defining a liquid passageway having a first opening into the lower portion of the compartment, such that the liquid passageway is in fluid communication with the lower portion of the compartment,
wherein the cartridge is attachable to at least one of a receptacle or a lid, the receptacle having a bottom wall structure closing a first end of the receptacle to delimit an inner material receiving space and having a receptacle opening at a second end of the receptacle that is opposite to the first end of the receptacle, the lid including a body structure having an outer periphery and defining a sample receiving opening and a second opening, the lid configured to close the receptacle opening such that the inner material receiving space is in fluid communication with the sample receiving opening,
wherein the cartridge is attachable to the at least one of the receptacle or the lid such that, based on the lid closing the receptacle opening such that the inner material receiving space is in fluid communication with the sample receiving opening,
the lower portion of the compartment is located closer to the first end of the receptacle than to the second end of the receptacle, and
the liquid passageway is in fluid communication with the second opening.

* * * * *